US006312396B1

(12) United States Patent
Müller

(10) Patent No.: US 6,312,396 B1
(45) Date of Patent: Nov. 6, 2001

(54) MASSAGING APPARATUS HAVING A SUCTION CHAMBER AND AT LEAST ONE ROLLER

(75) Inventor: Ingo Müller, Klagenfurt (AT)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/421,354

(22) Filed: Oct. 18, 1999

(30) Foreign Application Priority Data

Oct. 16, 1998 (EP) ................................................ 98890301

(51) Int. Cl.[7] ...................................................... A61M 7/00

(52) U.S. Cl. ...................... 601/6; 601/7; 601/9; 601/122; 601/125; 601/126; 601/133; 601/135

(58) Field of Search .................................. 601/6, 7, 8, 9, 601/10, 122, 123, 125, 126, 128, 129, 130, 133, 134, 135

(56) References Cited

U.S. PATENT DOCUMENTS 448,883 * 3/1891 Kahn .................................... 601/122
5,665,053 9/1997 Jacobs ...................................... 601/2
6,017,320 * 1/2000 Bleeker et al. ...................... 601/125
6,090,055 * 7/2000 Frajdenrajch ........................ 601/133

FOREIGN PATENT DOCUMENTS

0916330A1 5/1999 (EP) ............................ A61H/15/00
2057514 4/1971 (FR) ............................... A61H/7/00
98/02124 1/1998 (WO) ........................... A61H/15/00

* cited by examiner

*Primary Examiner*—Michael A. Brown
*Assistant Examiner*—Benjamin K. Koo
(74) *Attorney, Agent, or Firm*—Ernestine C. Bartlett; Norman N. Spain

(57) ABSTRACT

A massaging apparatus (1) comprising a housing (5) having a bottom wall (11) and a suction chamber (12) bounded by chamber walls (13, 14, 15, 16) and a pump (19) for the generation of a partial vacuum inside the suction chamber (12) and thus forming a skin fold (20) which is drawn into the suction space inside the suction chamber (12), as well as at least one roller (21, 22) to be placed onto a body area (3), comprises at least in an area of at least one wall (14), preferably a chamber wall (14), an apparatus part, preferably two cylinders (32, 33), which is movable with respect to this chamber wall (14), and these cylinders (32, 33) are movable, i.e. rotatable, with respect to the chamber wall (14) by the skin of the skin fold (20) drawn into the suction chamber (12), which results in only a comparatively low friction between the chamber wall (14) and the skin of the skin fold (20).

12 Claims, 2 Drawing Sheets

MASSAGING APPARATUS HAVING A SUCTION CHAMBER AND AT LEAST ONE ROLLER

BACKGROUND OF THE INVENTION

The invention relates to a massaging apparatus for massaging body areas of a person, which massaging apparatus comprises a housing having a bottom wall and can be placed onto the skin of a body area of a person with the bottom wall of the housing during a massaging session and is preferably movable over the skin in a given operating direction, during which a relative movement occurs between the skin and the bottom wall, and which comprises a suction chamber which encloses a suction space and which comprises two chamber walls which extend substantially transversely to the operating direction and two chamber walls which extend substantially parallel to the operating direction and are connected to the two chamber walls which extend transversely to the operating direction, and which is open in its area which faces the skin of a body area when the massaging apparatus is disposed on the skin with the bottom wall, and which comprises a pump which communicates with the suction chamber via an air-transfer duct so as to allow the passage of air and by means of which a partial vacuum can be generated inside the suction chamber when the massaging apparatus is disposed on the skin of a body area with its bottom wall, in order to forma skin fold which is drawn into the suction chamber, a relative movement being produced between the skin of the skin fold and at least one chamber wall, and which in the area of the bottom wall comprises at least one roller which is rotatable about a roller axis which extends transversely to the operating direction and which can be placed onto the skin of a body area with its circumferential surface.

Such a massaging apparatus of the type defined in the opening paragraph is known, for example, from the patent document WO 98/02124 A1. In said known massaging apparatus the bottom wall of the housing is comparatively smooth in order to preclude irritation of the skin and both the chamber walls which extend transversely to the operating direction and the chamber walls which extend parallel to the operating direction have a steady curvature and the bounding surfaces of the chamber walls which face the suction space have a given roughness, which lies preferably in a range between 4 $\mu$m and 8 $\mu$m. Owing to this construction of the known massaging apparatus it has been found that comparatively high friction values occur between the bottom wall of the housing and the skin and between at least one of the chamber walls and the skin of the skin fold which is drawn into the suction chamber, as a result of which, owing to the comparatively high friction values, the further movement of the massaging apparatus in the operating direction is hindered and, owing to the comparatively high friction values, a relatively great force is exerted on the skin fold drawn into the suction chamber, which is at least to some extent experienced as unpleasant or even painful.

SUMMARY OF THE INVENTION

It is an object of the invention to preclude the above-mentioned problems and to provide an improved massaging apparatus of the type defined in the opening paragraph, in which the afore-mentioned problems are solved by simple means. To achieve this object, according to the invention, a massaging apparatus of the type defined in the opening paragraph is characterized in that at least in an area of at least one wall of the massaging apparatus, in which area a relative movement is produced between the skin and this wall, at least one apparatus part which is movable with respect to this wall is provided, and the location of the at least one apparatus part on this wall 14 is selected in such a manner that, as the massaging apparatus is moved over the skin of a body area and thus a skin fold is drawn into the suction chamber, the at least one apparatus part is movable with respect to this wall by the skin.

By taking the steps in accordance with the invention it can be achieved in a very simple manner that no high friction values occur between the bottom wall of the housing and the skin and between the skin surface of the skin fold drawn into the suction chamber and the inner bounding surface of the suction chamber, because the at least one apparatus part which has been provided in the area of at least one wall of the massaging apparatus and which is movable with respect to this wall provides a distinct reduction of the friction between the skin and the relevant wall, as a result of which a smooth further movement of the massaging apparatus in the operating direction is guaranteed during a massaging session and no undesirable or painful forces are exerted on the skin fold which has been drawn into the suction chamber or such forces are reduced to such an extent that no adverse effect is produced.

In a massaging apparatus in accordance with the invention balls may be used as apparatus parts which are movable with respect to a wall, which balls are mounted in ball cages provided in the relevant wall. Alternatively, such movable apparatus parts can be, for example, endless loops or belts wrapped around two rotatably supported guide rollers.

In a massaging apparatus in accordance with the invention such movable apparatus parts such as balls may be provided in the area of the bottom wall of the housing. However, it has proved to be very advantageous if at least one of such apparatus part is provided in an area of at least one chamber wall of the suction chamber. In this respect, it has proved to be particularly advantageous if the at least one part which is movable with respect to a chamber wall is formed by at least one cylinder, because this is constructionally very simple and constructionally advantageous and because such a solution has proved to be very reliable and insensitive to soiling effects.

In a massaging apparatus in accordance with the invention at least one cylinder may be provided in an area of the chamber wall which extends transversely to the operating direction and which is situated in front in relation to the operating direction or at least one cylinder may be provided in an area of each of the two chamber walls which extend transversely to the operating direction. It has proved to be particularly advantageous if at least one cylinder is provided in an area of the chamber wall which extends transversely to the operating direction and which is situated at the rear in relation to the operating direction, because this enables the friction to be reduced most effectively. For a satisfactory compromise between the required space and a maximal reduction of the friction it has proved to be particularly advantageous if two cylinders arranged in tandem are provided. It is obvious that also more than two cylinders may be provided.

Each cylinder may be disposed so as to extend substantially tangentially with respect to the bounding surface of the relevant chamber wall with its circumferential surface. However, it has proved to be advantageous if each cylinder projects with its circumferential surface into the suction space to at least a small extent.

The measures defined in claims 9, 10, 11 and 12 have proved to be particularly advantageous in a massaging apparatus in accordance with the invention. This is because, as a result of these measures, the formation of a skin fold, which is basically effected by virtue of the suction effect in the suction space, is enhanced by at least the forward roller, as viewed in the operating direction, and because, in addition, the driving of the massaging apparatus on the skin of a body area is enhanced effectively by at least the forward roller, as viewed in the operating direction. It is to be noted that tests have revealed that for the circumferential surface of the forward roller, as viewed in the operating direction, a material having a hardness of approximately 85 Shore A and for the circumferential surface of the rearward roller, as viewed in the operating direction, a material having an indentation hardness in accordance with ISO 2039 of approximately 144 N/mm$^2$ have proved to be very favorable.

The afore-mentioned as well as further aspects of the invention will be apparent from the embodiment described hereinafter by way of example and will be elucidated with reference to this example.

BRIEF DESCRIPTIONS OF THE DRAWINGS

The invention will now be described in more detail with reference to the drawings, which show an embodiment given by way of example, to which the invention is not limited.

DESCRIPTION OF THE PREFERRED EMBODIMENTS

Figure 1:
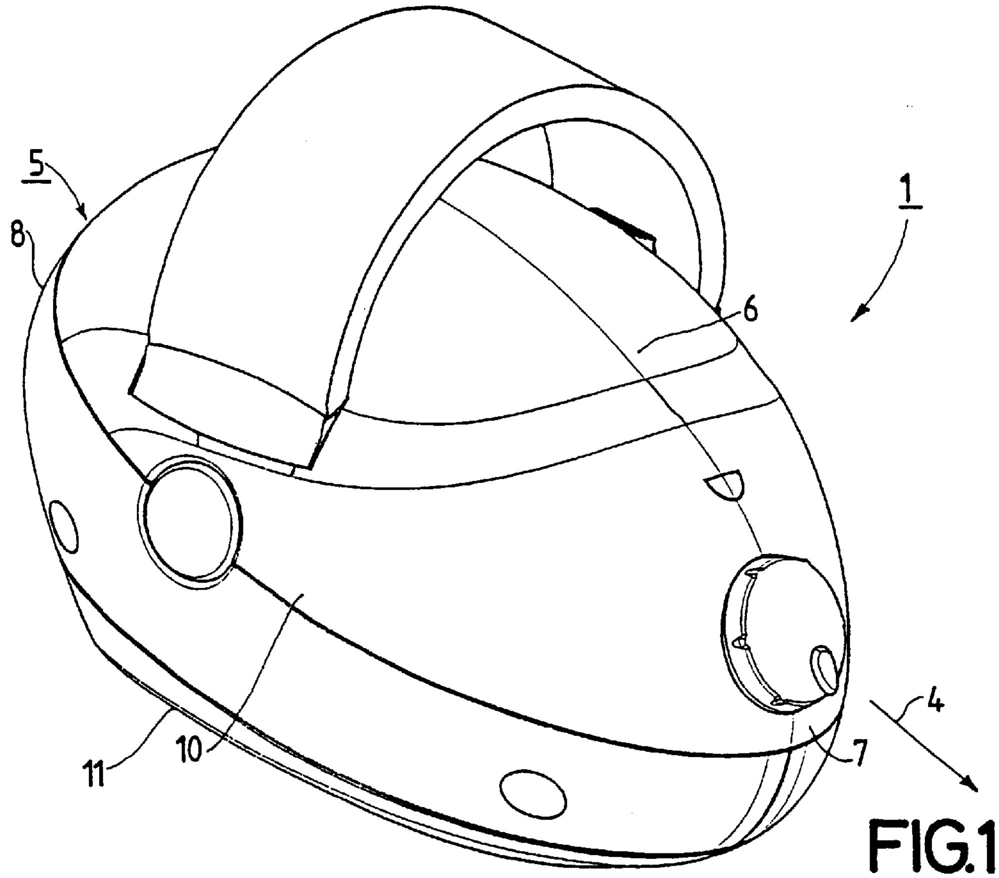
FIG. 1 is an oblique top view showing a massaging apparatus in accordance with an embodiment of the invention.
Figure 2:
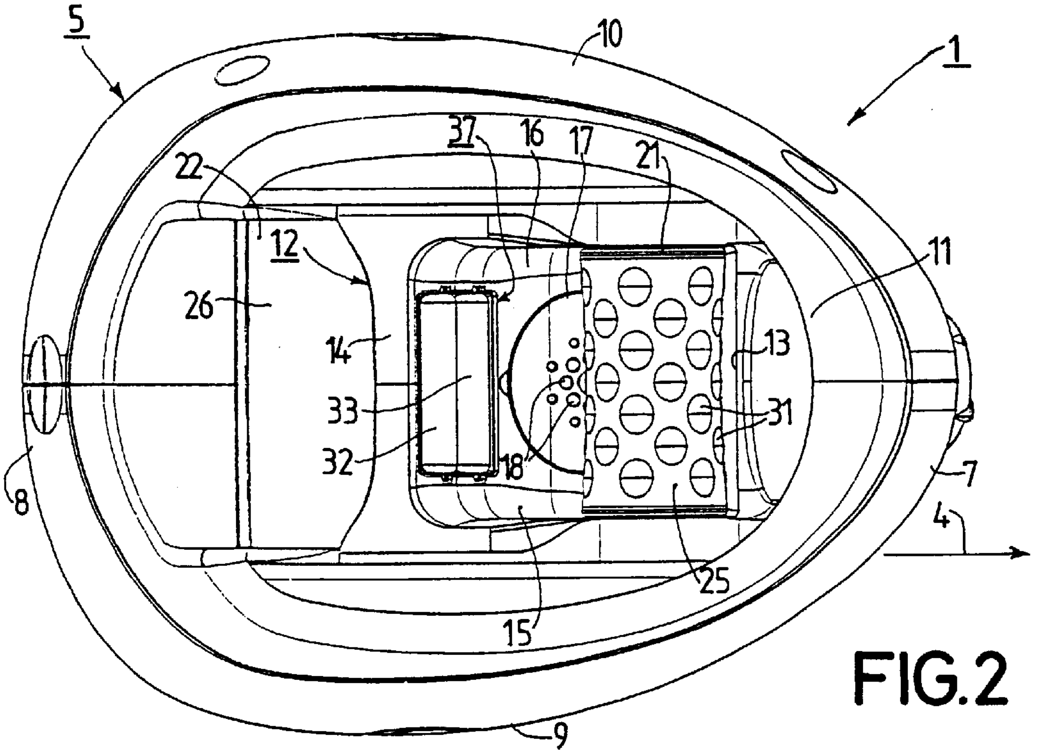
FIG. 2 shows the massaging apparatus of FIG. 1 in an underneath view.
Figure 3:
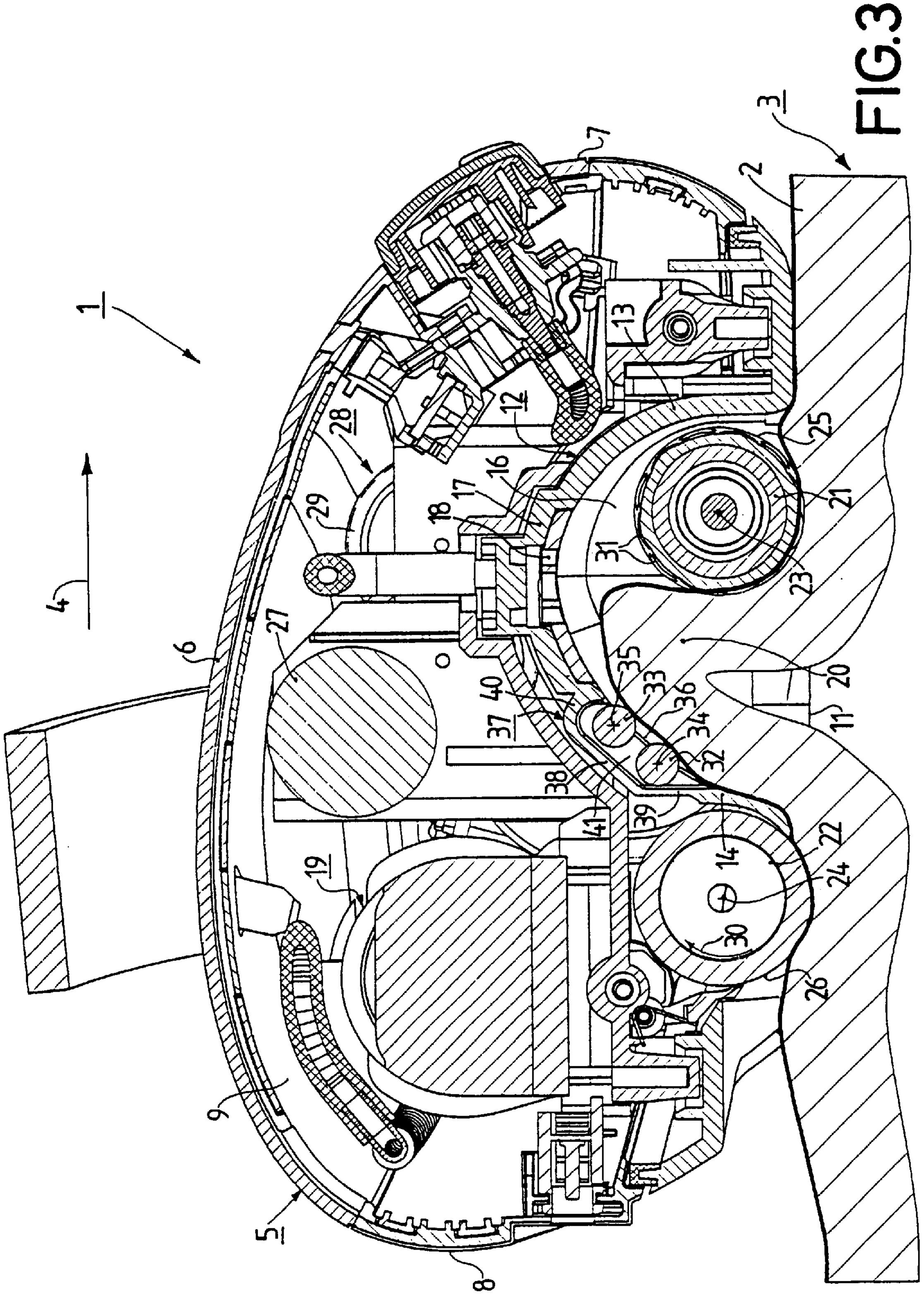
FIG. 3 shows the massaging apparatus of FIGS. 1 and 2 in a sectional view and also shows diagrammatically a skin fold formed during a massaging session.

FIGS. 1 to 3 show a massaging apparatus 1 intended for massaging body areas of a person. During a massaging session the massaging apparatus 1 can be placed onto a body area 3 of a person, as is shown diagrammatically in FIG. 3. During such a massaging session the massaging apparatus 1 is preferably movable over the skin 2 in a given operating direction, which operating direction is indicated by an arrow 4 in FIGS. 1 to 3. As regards the design and construction of the massaging apparatus 1 reference can be made to the patent document WO 98/02124 A1 already mentioned in the introductory part, which document is herewith incorporated by reference. In view of the detailed description of the known massaging apparatus disclosed in the patent document WO 98/02124 A1 the present Application only gives a detailed description of those design and construction features which differ from the known massaging apparatuses and which are relevant in the present context.

The massaging apparatus 1 comprises a housing 5 having an upper wall 6 and four side walls, namely a front side wall 7, a rear side wall 8, a left-hand side wall 9 and a right-hand side wall 10. The housing 5 has a bottom wall 11 at its side opposite to the upper wall 6.

The massaging apparatus 1 has a suction chamber 12 which encloses a suction space and which comprises two chamber walls 13 and 14 which extend substantially transversely to the operating direction 4 and which further comprises two chamber walls 15 and 16 which extend substantially parallel to the operating direction 4 and are connected to the two chamber walls 13 and 14 which extend transversely to the operating direction 4. The suction chamber 12 is open at the location which faces the skin 2 of a body area 3 when the massaging apparatus 1 is placed on the skin 2 with the bottom wall 11, i.e. at the location of the bottom wall 11. At the side opposite the open side the suction chamber 12 is closed by an upper chamber wall 17. The upper chamber wall 17 has passages 18 which are connected to a pump 19 via an air-transfer duct, which for reasons of simplicity is not shown in FIG. 3, so that the pump 19 communicates with the suction chamber 12 so as to allow the passage of air via the air-transfer duct, not shown.

When the massaging apparatus 1 has been placed with its bottom wall 11 onto the skin 2 of a body area 3 the pump 19 can generate a partial vacuum inside the suction chamber 12 in order to draw a skin fold 20 into the suction chamber, as is shown in FIG. 3. Once such a skin fold 20 has been drawn into the suction space of the suction chamber 12 a relative movement is possible between the skin of the skin fold 20 and the chamber wall 14. Such a relative movement occurs when the massaging apparatus 1 is moved over the skin 2 of a body area 3 in the operating direction 4. During such a movement of the massaging apparatus 1 over the skin 2 of a body area 3 the skin fold 20 formed moves further in the operating direction 4, which produces a massaging effect.

In the area of the bottom wall 1 the massaging apparatus 1 further comprises two rollers 21 and 22, which are each rotatable about a respective roller axis 23 or 24 which extends transversely to the operating direction 4 and which can be placed onto the skin 2 of a body area 3 with their respective circumferential surfaces 25 and 26. Of the two rollers 21 and 22 the forward roller 21, as viewed in the operating direction 4, is disposed inside the suction chamber 12 and the rearward roller 22, as viewed in the operating direction 4, is disposed outside the suction chamber 12, as is apparent in particular from FIG. 3.

In the massaging apparatus 1 the two rollers 21 and 22 can be driven by a motor 28, which drives the two rollers 21 and 22 via a drive transmission 28, of which only an intermediate gear wheel 29 is visible in FIG. 3. The two rollers 21 and 22 can be driven in the same direction of rotation, as indicated for the roller 22 by means of an arrow 30 in FIG. 3. The same direction of rotation 30 for the two rollers 21 and 22 is defined in such a manner that the speed vectors of the circumferential areas of the circumferential surfaces 25 and 26 of the two rollers 21 and 22, which face the skin 2 with the massaging apparatus 1 placed on the skin 2 of a body area 3, are oriented oppositely to the operating direction 4. Owing to this direction of rotation of the two rollers 21 and 22 the massaging apparatus 1 is driven in the operating direction 4 with the aid of the two rollers 21 and 22 by cooperation with the skin 2 of a body area 3.

In the massaging apparatus 1, in order to guarantee optimum driving of the massaging apparatus 1 by means of the two rollers 21 and 22, the circumferential surface 25 of the forward roller 21, as viewed in the operating direction 4, consists of a comparatively soft material having a hardness in a range between 40 Shore A and 95 Shore A, a value of approximately 85 Shore A having proved to be very favorable in practice. Furthermore, in the massaging apparatus 1 the circumferential surface 26 of the rearward roller 22, as viewed in the operating direction 4, consists of a comparatively hard material having an indentation hardness in a range between 50 N/mm$^2$ and 180 N/mm$^2$ determined with a test load of 358 N and a test time of 30 seconds in accordance with ISO 2039, a value of approximately 144 N/mm$^2$ having proved to be very favorable in practice.

Moreover, in the massaging apparatus 1 the circumferential surface 25 of the forward roller 21, as viewed in the operating direction 4, is given a slightly concave shape and is provided with a multitude of studs 31, as is apparent in particular from FIG. 2. Furthermore, in the massaging apparatus 1 the circumferential surface 26 of the rearward roller 22, as viewed in the operating direction 4, is given a smooth shape.

The implementation of the circumferential surfaces 25 and 26 of the two rollers as described in the foregoing, not only results in the massaging apparatus 1 being driven satisfactorily in order to move it over the skin 2 of a body area 3 but, in addition, it also enhances the formation of a skin fold 20 in an advantageous manner.

Furthermore, for effectively assisting in the formation of a skin fold 20 in the massaging apparatus 1 the forward roller 21, as viewed in the operating direction 4, may be driven with a slightly higher speed than the rearward roller 22, as viewed in the operating direction, as a result of which the rearward roller 22 in relation to the forward roller 21 exerts a slight braking action on the skin 2 of a body area 3, which has a favorable effect on the formation of a skin fold 20.

As already stated hereinbefore, a relative movement occurs between the skin of the skin fold 20 and at least one chamber wall during a massaging session, in the present massaging apparatus particularly the chamber wall 14 but also the two chamber walls 15 and 16. In the massaging apparatus 1 it has therefore proved to be very advantageous if at least in an area of at least one chamber wall, in the present case in an area of the chamber wall 14 which extends transversely to the operating direction 4 and which is situated at the rear as seen in the operating direction 4, in which area a relative movement between the skin fold 20 and the chamber wall 14 is possible, at least one apparatus part which is movable relative to the chamber wall 14, in the present case at least one cylinder, is provided. In the massaging apparatus 1 two cylinders arranged in tandem are provided in the area of the chamber wall 14, which cylinders are rotatable about respective roller axes 34 and 35 which extend transversely to the operating direction 4, the two cylinder axes 34 and 35 extending parallel to the two roller axes 23 and 24 of the two rollers 21 and 22.

As is apparent from FIG. 3, the location of the at least one apparatus part which is movable with respect to the chamber wall 14, i.e. the location of the two cylinders 32 and 33, is selected in such a manner that, as the massaging apparatus 1 is moved over the skin 2 of a body area 3 and thus a skin fold is drawn into the suction chamber 12, the at least one apparatus part, i.e. the two cylinders 32 and 33, is movable with respect to the chamber wall 14 by the skin of the skin fold 20. In the present case the two cylinders 32 and 33 are rotationally driven by the skin of the skin fold 20 in the direction indicated by the arrow 30 during a massaging session. In order to achieve that this rotational drive of the two cylinders 32 and 33 with the aid of the skin of the skin fold is effected in an effective manner, the two cylinders 32 and 33 in the massaging apparatus 1 each project with their respective circumferential surfaces into the suction space bounded by the suction chamber 14 beyond the bounding surface 36 of the chamber wall 14 facing the suction space. In order to accommodate the two cylinders 32 and 33 the massaging apparatus 1 has a recess 37 in the area of the chamber wall 14, which recess is open towards the suction space enclosed by the suction chamber 12 and for the remainder is bounded by recess walls 38, 39, 40 and 41 which are connected to the chamber wall 14. The two cylinders 32 and 33 are for the greater part disposed in this recess.

The provision of the two cylinders 32 and 33, which are rotationally drivable by the skin of the skin fold 20 formed during a massaging session, advantageously ensures that now a sliding friction occurs between a small area of the chamber wall 14 and the skin fold 20 then formed, while as a result of the provision of the two cylinders 32 and 33 in the remaining area only a rolling friction occurs between the two cylinders 32 and 33 and the skin fold 20 which is formed, the resulting friction between the skin of the skin fold 20 and the apparatus parts and apparatus areas which cooperate with the skin of the skin fold 20 being distinctly smaller as compared with a massaging apparatus having no such cylinders. As a result of this, the massaging apparatus 1 as shown in FIGS. 1 to 3 can be moved comparatively smoothly over the skin 2 of a body area 3 of a person.

In the massaging apparatus 1 it is also possible to provide small cylinders or balls in the area of the bottom wall 11 of the housing 5 in order to reduce the friction between the skin and the bottom wall 11. However, the massaging apparatus 1 does not use this possibility because in the present case the bottom wall 11 has a comparatively small surface area.

What is claimed is:

1. A massaging apparatus for massaging body areas of a person, which massaging apparatus comprises a housing having a bottom wall and can be placed on the skin of a body area of a person with the bottom wall of the housing contacting the skin during a massaging session and is moved over the skin in a given operating direction, during which a relative movement occurs between the skin and the bottom wall, and which apparatus comprises a suction chamber which encloses a suction space and which comprises two chamber walls which extend substantially transversely to the operating direction and two chamber walls which extend substantially parallel to the operating direction and are connected to the two chamber walls which extend transversely to the operating direction, and which is open in its area which faces the skin of a body area when the m assaging apparatus is disposed on the skin with the bottom wall, and which comprises a pump which communicates with the suction chamber via an air-transfer duct for generating a partial vacuum inside the suction chamber when the massaging apparatus is disposed on the skin of a body area with its bottom wall, thereby forming a skin fold which is drawn into the suction chamber, a relative movement being produced between the skin of the skin fold and one of the chamber walls which extend transversely to the operating direction, and which in the area of the bottom wall comprises at least one roller which is rotatable about a roller axis which extends transversely to the operating direction and which at least one roller contacts the skin of a body area with its circumferential surface, wherein at least in an area of said one of the chamber wails which extend transversely to the operating direction, in which area a relative movement is produced between the skin and said one of the chamber walls, at least one skin contacting means which is movable with respect to said one of the chamber walls is provided, and the location of the at least one skin contacting means on said one of the chamber walls is selected in such a manner that, as the massaging apparatus is moved over the skin of a body area and a resultant skin fold is drawn into the suction chamber, the at least one skin contacting means is moved with respect to said one of the chamber walls by the skin.

2. A massaging apparatus as claimed in claim 1, wherein at least one skin contacting means which is movable with respect to said one of the chamber walls is provided at least in an area of said one chamber walls of the suction chamber.

3. A massaging apparatus as claimed in claim 2, wherein the at least one skin contacting means comprises at least one cylinder which is rotatable about a cylinder axis which extends transversely to the operating direction.

4. A massaging apparatus as claimed in claim 3, wherein at least one cylinder is provided in an area of said one of the chamber walls, which area extends transversely to the operating direction (4) and is situated at the rear, as viewed in the operating direction.

5. A massaging apparatus as claimed in claim 3, wherein two cylinders arranged in tandem are provided in said area of said one of the chamber walls.

6. A massaging apparatus as claimed in claim 3, wherein said at least one cylinder projects with its circumferential surface into the suction space beyond said one of the chamber walls which faces the suction space.

7. A massaging apparatus as claimed in claim 3, wherein in the area of said one of the chamber walls in which at least one cylinder is disposed, a recess is provided which is open towards the suction space and which for the remainder is bounded by recess walls which are connected to said one of the chamber walls, which recess accommodates at least the greater part of the at least one cylinder.

8. A massaging apparatus as claimed in claim 3, wherein the roller axis of the at least one roller and the cylinder axis of the at least one cylinder extend parallel to one another.

9. A massaging apparatus (1) as claimed in claim 1, wherein one of the two rollers is disposed at the front, as viewed in the operating direction, and is arranged inside the suction chamber, and the other of the two rollers is disposed at the rear, as viewed in the operating direction, and is arranged outside the suction chamber.

10. A massaging apparatus as claimed in claim 9, wherein both rollers can be driven in the same direction of rotation by means of a motor via a drive transmission, the speed vectors of the circumferential areas of the circumferential surfaces of the two rollers, which face the skin of a body area when the massaging apparatus is disposed on the skin being oriented oppositely to the operating direction.

11. A massaging apparatus as claimed in claim 10, wherein the circumferential surface of the roller which is disposed at the front, as viewed in the operating direction, consists of a comparatively soft material having a hardness in a range between 40 Shore A and 95 Shore A, and the circumferential surface of the roller which is disposed at the rear, as viewed in the operating direction, consists of a comparatively hard material having an indentation hardness in a range between 50 $N/mm^2$ and 180 $N/mm^2$ determined with a test load of 358 N and a test time of 30 seconds in accordance with ISO 2039.

12. A massaging apparatus as claimed in claim 11, wherein the circumferential surface of the roller which is disposed at the front, as viewed in the operating direction, has a multitude of studs, and the circumferential surface of the roller which is disposed at the rear, as viewed in the operating direction has a smooth shape.

* * * * *